(12) United States Patent
Cho et al.

(10) Patent No.: US 11,752,270 B2
(45) Date of Patent: Sep. 12, 2023

(54) SYRINGE WITH PLUNGER REACTION PRESSURE REDUCTION STRUCTURE

(71) Applicant: PoongLim Pharmatech Inc., Gunsan (KR)

(72) Inventors: Hee Min Cho, Gunsan (KR); Mi Heui Cho, Gunsan (KR); Jong Deok Yun, Gunsan (KR); Jae Cheon Kim, Jeonju (KR)

(73) Assignee: POONGLIM PHARMATECH INC., Gunsan (KR)

( * ) Notice: Subject to any disclaimer, the term of this patent is extended or adjusted under 35 U.S.C. 154(b) by 29 days.

(21) Appl. No.: 17/193,144

(22) Filed: Mar. 5, 2021

(65) Prior Publication Data

US 2022/0203037 A1 Jun. 30, 2022

(30) Foreign Application Priority Data

Dec. 29, 2020 (KR) .......................... 10-2020-0186182

(51) Int. Cl.
*A61M 5/315* (2006.01)
*A61M 5/31* (2006.01)
*A61M 5/34* (2006.01)

(52) U.S. Cl.
CPC ...... *A61M 5/31511* (2013.01); *A61M 5/3137* (2013.01); *A61M 5/347* (2013.01); *A61M 2005/31516* (2013.01); *A61M 2005/31523* (2013.01)

(58) Field of Classification Search
CPC ............ A61M 5/31511; A61M 5/3137; A61M 5/347; A61M 2005/31516; A61M 2005/31523
See application file for complete search history.

(56) References Cited

U.S. PATENT DOCUMENTS

2004/0230159 A1* 11/2004 Chao ...................... A61M 5/322
604/110

FOREIGN PATENT DOCUMENTS

| KR | 20-0451044 Y1 | 11/2010 |
| KR | 20-0467647 Y1 | 6/2013 |

* cited by examiner

*Primary Examiner* — Bhisma Mehta
*Assistant Examiner* — Hong-Van N Trinh
(74) *Attorney, Agent, or Firm* — KORUS Patent, LLC; Seong Il Jeong

(57) ABSTRACT

A syringe with plunger reaction pressure reduction structure is proposed. The syringe includes: a barrel including a finger grip at a rear end thereof and a Luer-lock connector in which a thread portion is formed on an inner surface outside a tapered tube of a front discharge end thereof; a plunger rod configured to be inserted in an inside of the barrel and including a push end at a rear end thereof; a plunger coupled to a front end of the plunger rod; and a needle hub configured to be screwed with the Luer-lock connector and including an injection needle mounted to a front end thereof. The syringe is configured to have a three-step structure at the plunger in which intervals between steps are gradually shortened, so that the reaction pressure applied to the plunger is distributed and the injection is easily performed.

3 Claims, 5 Drawing Sheets

SYRINGE WITH PLUNGER REACTION PRESSURE REDUCTION STRUCTURE

CROSS REFERENCE TO RELATED APPLICATION

The present application claims priority to Korean Patent Application No. 10-2020-0186182, filed Dec. 29, 2020, the entire contents of which is incorporated herein for all purposes by this reference.

BACKGROUND OF THE INVENTION

Field of the Invention

The present disclosure relates generally to a syringe with a plunger reaction pressure reduction structure and, more particularly, to a syringe with a plunger reaction pressure reduction structure, which is configured to reduce reaction pressure applied to a plunger when injection liquid is injected into a patient with the syringe and the injection is almost completed so that the injection is completed easily without remaining injection liquid.

Description of the Related Art

In general, syringes are classified into a general type syringe and a Luer-lock type syringe. The general type syringe includes a barrel as a main body of a syringe, a push rod with a finger grip, a plunger fastened to a front end of the push rod and pushing injection liquid in a piston manner, and an injection needle fastened to a tapered tube at a front end of the barrel, and the Luer-lock type syringe has a structure in which a separate Luer-lock connector is provided to be screwed to the front end of the barrel and a hub to which the injection needle is mounted is screwed to the Luer-lock connector.

In the syringe configured as described above, the plunger made of rubber or silicone is mounted by being fitted over an end of the push rod. In general, the shape of a front end of the plunger is formed in a horizontal surface or a slight conical shape, so injection liquid remaining in the tapered tube formed at an end of the barrel cannot be discharged from the syringe and is disposed of while remaining in the syringe. When the plunger reaches the front end of the barrel, the injection liquid should pass through an inner diameter of the injection needle, which is relatively smaller than a diameter of the barrel, so that the plunger is subjected to an increasingly larger reaction pressure due to the bottleneck state. Therefore, it is difficult for medical staff to push injection liquid to the end of the barrel, when multiple injections are required, the medial staff becomes fatigued, and when a viscous injection liquid is injected, it takes more hand force to push the injection liquid, so female nurses with weak finger grips have difficulty and patients feel pain.

As an example, Korean Utility Model Registration No. 20-0467647 "Syringe" was disclosed. In the syringe of the related art, two pistons are provided as plungers and a partition piston is inserted at a distance from a main piston fastened to a piston rod. When different injection liquids are filled at a distance from each other and the piston rod is pressed, the partition piston is pressed and moved together with the main piston pressed, injection liquid filled in a front portion of the barrel is moved and mixed with injection liquid in a lower portion thereof through a moving portion, and the mixed injection liquid is moved and pressed toward a plug at a front end of the barrel and is injected by being discharged through the injection needle.

However, the syringe of the related art is also configured such that the front end of the piston that is provided as a plunger is formed in a plane with no different from conventional syringes. Therefore, when injection liquid is moved toward the front plug of the barrel, reaction pressure is applied even stronger, and two pistons require more pressure, so it is difficult for nurses having weak hand force to use the syringe.

As another example, Korean Utility Model Registration No. 20-0451044 "Auto disable syringe with structure preventing from turning of plunger" is disclosed. The syringe of the related art is the Luer-lock type syringe, and is configured such that a tip at a front end of a barrel is formed in a long shape so as to be inserted into a needle holder, a gasket that is provided as a plunger is formed to be fitted in a ring shape to a gasket support, and a protrusion having a step protrudes on a front end of the gasket support. An elastic piece is provided inside a skirt tip, so that the protrusion can enter the front end portion of the barrel while pushing an elastic piece, but removal of the protrusion is prevented after the injection is completed, so that the used syringe cannot be reused.

However, the Luer-lock type syringe of the related art is also configured such that a front portion of the gasket that is provided as a plunger is formed in a plane. Therefore, when injection liquid is moved toward the skirt tip, reaction pressure is applied strongly, thus it takes a lot of effort to discharge the entire amount injection liquid from the barrel.

In view of the above the problems, a tapered and long conical plunger is proposed. In this structure, injection liquid can be fully pushed to the end so that the injection liquid does not remain in the syringe. However, reaction pressure is evenly applied to the inside of the syringe, so reaction pressure of the plunger is increased when the plunger reaches a point where injection liquid is fully pushed.

DOCUMENTS OF RELATED ART (Patent Document 1) Korean Utility Model Registration No. 20-0467647 (Jun. 19, 2013); and (Patent Document 2) Korean Utility Model Registration No. 20-0451044 (Nov. 15, 2010)

SUMMARY OF THE INVENTION

Accordingly, the present disclosure has been made keeping in mind the above problems occurring in the related art, and the present disclosure is intended to propose a syringe with a plunger reaction pressure reduction structure, wherein, the syringe is configured such that, the inside shape of a tapered tube formed on a front discharge end of a barrel and the outside shape of a plunger are formed in long tapered shapes, and respectively have three-step structures in which intervals between steps are gradually shortened and diameters of the steps become small as the tapered tube and the plunger go frontward, so that the reaction pressure applied to the plunger is distributed to allow the injection to be easily performed.

In order to achieve the above objective, according to one aspect of the present disclosure, there is provided a syringe with a plunger reaction pressure reduction structure of the present disclosure. In the syringe, a plunger may be formed in a long conical shape and have a three-step structure in which a diameter thereof may be gradually narrowed and intervals between steps may be gradually shortened as the plunger goes toward an end thereof, and corresponding to the structure of the plunger, a tapered tube, which may receive the plunger, of a front discharge end of a barrel may have three-step grooves in which an inner diameter thereof may be gradually narrowed and intervals between the grooves may be gradually shortened as the tapered tube goes frontward, and the steps of the plunger may be coupled to the grooves in the tapered tube, so that reaction pressure further applied to the plunger as the plunger goes to the end of the discharge may be distributed in order to enable the injection to be performed without an effort and injection liquid remaining in the syringe.

In the present disclosure, the plunger of the syringe has multi-layer steps in which diameters of steps are gradually narrowed and intervals between the steps are shortened as the plunger goes frontward. Corresponding to the plunger, the tapered tube of the front discharge end of the barrel has three-step grooves in which inner diameter of the grooves are narrowed and intervals between grooves are shortened as the barrel goes frontward, so that the steps of the plunger and the grooves of the barrel are fastened to each other. Whereby, the reaction pressure applied to the plunger from the start of the injection to the end thereof can be minimized and the entire amount of injection liquid can be injected without injection liquid remaining. As an example, when multiple injections are performed in succession to many people, such as the injection of Coronavirus vaccine, medical staff can perform injections without becoming fatigued, and the entire amount of injection liquid can be injected without the problem that precious medicinal liquid is discharged and is discarded. The device of the present disclosure can be effectively applied to a syringe used to inject injection liquid such as high-viscosity bone injection liquid.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
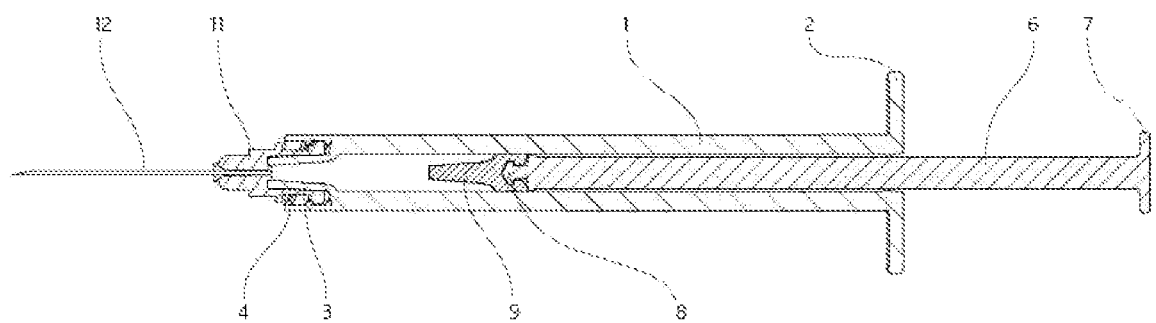
FIG. 1 is a sectional view showing an assembled state of a syringe with a plunger reaction pressure reduction structure according to the present disclosure.
Figure 2:
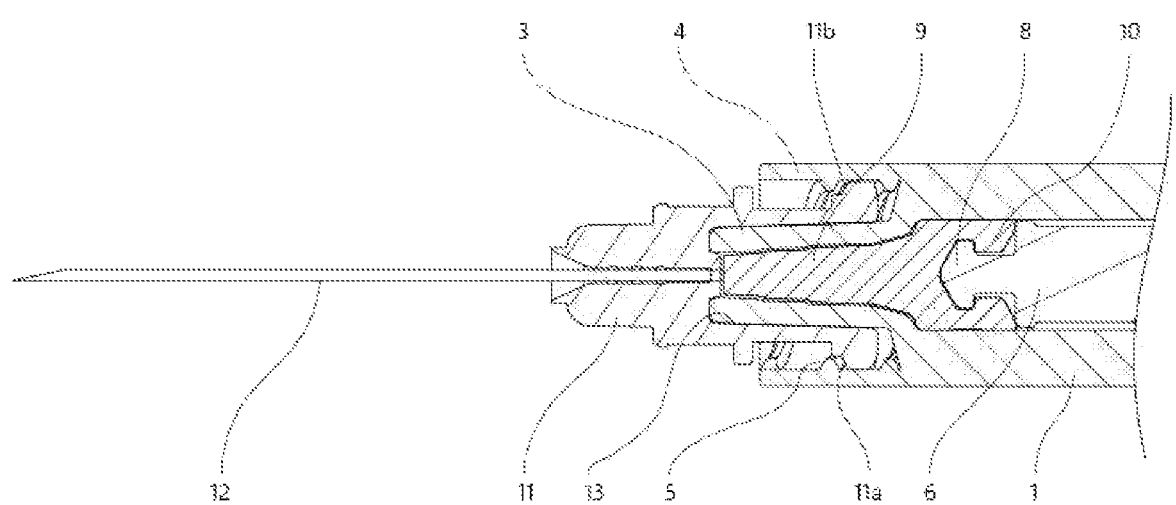
FIG. 2 is a partially enlarged sectional view showing the assembled state of the syringe with the plunger reaction pressure reduction structure according to the present disclosure.
Figure 3:
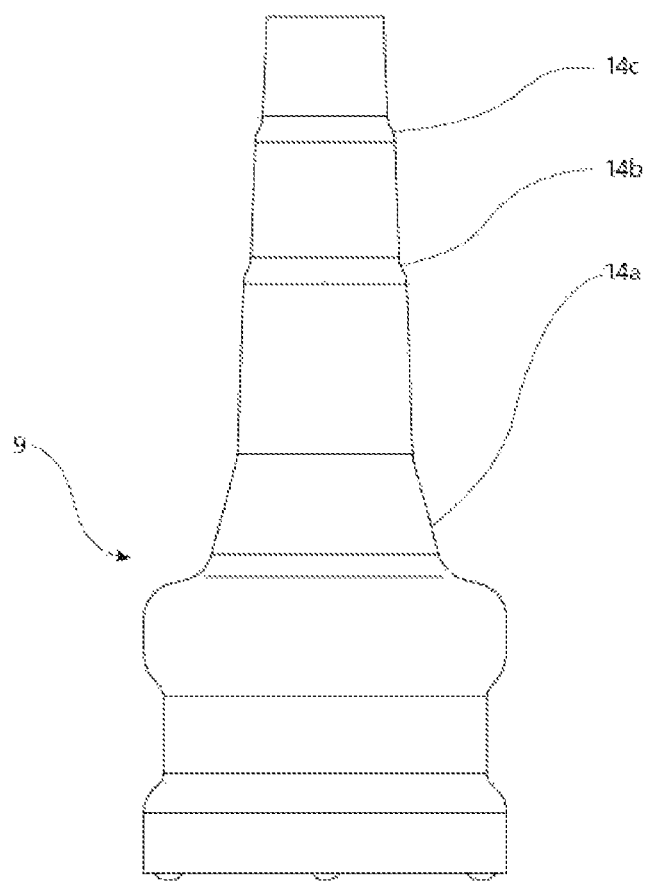
FIG. 3 is a front view showing a plunger of the syringe with the plunger reaction pressure reduction structure according to the present disclosure.
Figure 4:
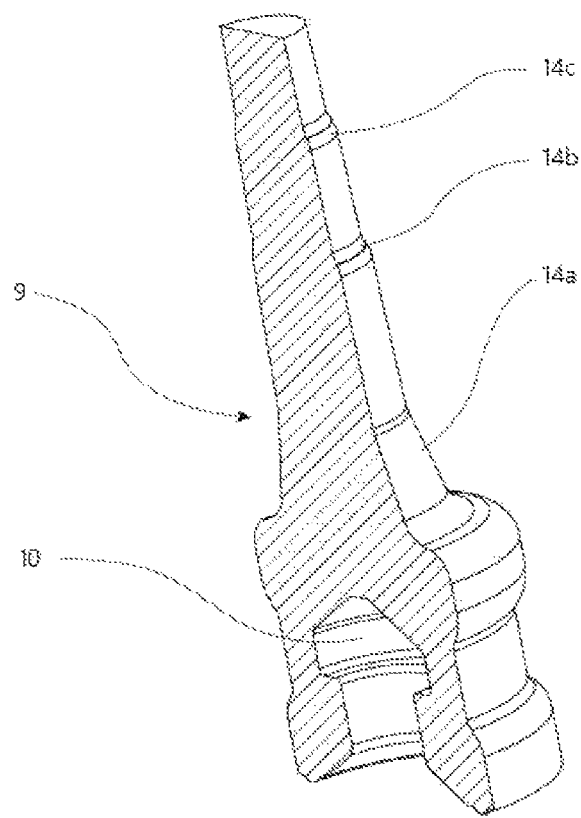
FIG. 4 is a 3D sectional view showing the plunger of the syringe with the plunger reaction pressure reduction structure according to the present disclosure.
Figure 5:
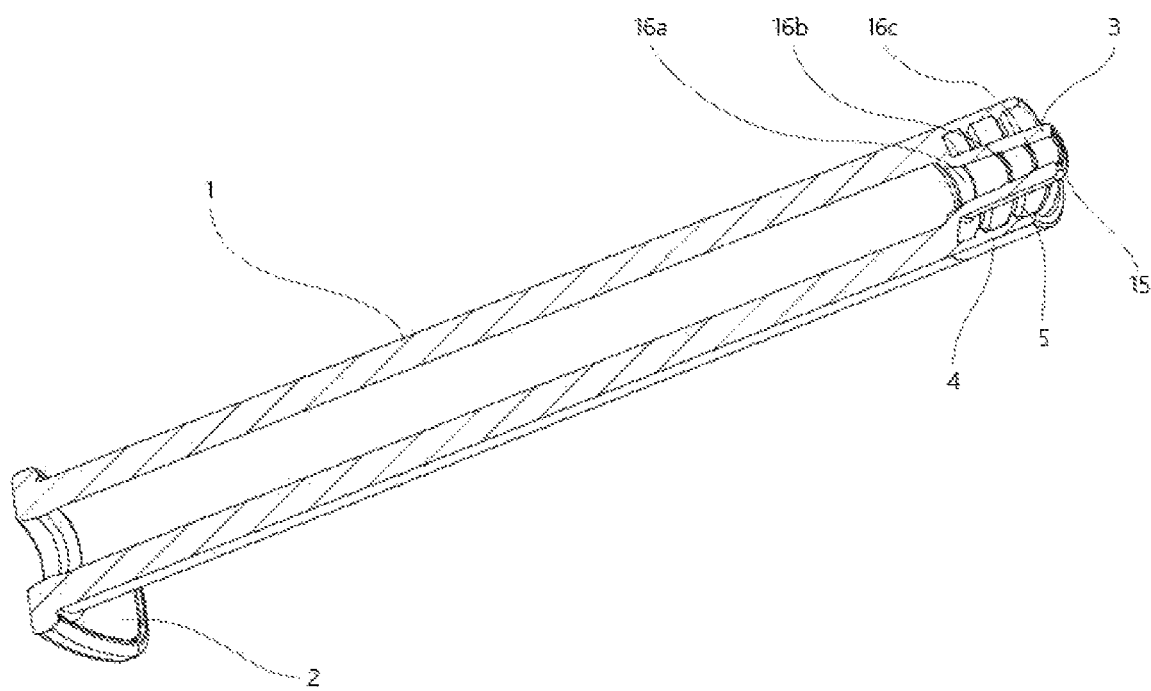
FIG. 5 is a 3D sectional view showing a barrel of the syringe with the plunger reaction pressure reduction structure according to the present disclosure.

The above and other objectives, features, and advantages of the present disclosure will be more clearly understood from the following detailed description taken in conjunction with the accompanying drawings.

In the flowing description, unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinbelow, a syringe with a plunger reaction pressure reduction structure according to an exemplary embodiment of the present disclosure will be described in detail with reference to accompanying drawings.

As shown in the drawings, the syringe with the plunger reaction pressure reduction structure of the present disclosure is configured as a general Luer-lock type syringe. In the syringe, a barrel 1 has a finger grip 2 at a rear end thereof and a Luer-lock connector 4 in which a thread portion 5 is formed on an inner surface outside a tapered tube 3 of a front discharge end thereof, and a plunger rod 6 having a push end 7 at a rear end thereof is inserted into the barrel 1. Whereby, a plunger fastening protrusion 8 formed on a front end of the plunger rod 6 is fitted into a plunger fastening closed hole 10 formed inside a rear end of a plunger 9 to couple the plunger rod 6 to the plunger 9.

Meanwhile, fastening protruding steps 11a and 11b, which are formed by protruding on opposite sides of a rear end of a needle hub 11 to correspond to the thread portion 5 of the Luer-lock connector 4 formed on a front end of the barrel 1, pass through and join to the thread portion 5, so that the needle hub 11 is fastened to the barrel 1. An injection needle 12 is fastened to an upper end of the needle hub 11 by passing through the inside of the needle hub 11. An insertion hole 13 for the tapered tube of the barrel is formed in a rear portion of the needle hub 11. The tapered tube 3 of the barrel 1 is inserted into the insertion hole 13 with the screwing and Luer-lock fastening of the needle hub 11, so that the needle hub 11 with the injection needle 12 and the barrel 1 are fastened to each other.

In forming the plunger 9 of the above-described structure, the plunger 9 is formed in a long tapered conical shape made of rubber or silicone, the plunger 9 consists of a three-step structure in which an outer diameter of the plunger 9 is gradually reduced and intervals 18a and 18b between steps are shortened as the plunger goes frontward to a first step 14a, a second step 14b, and a third step 14c. Corresponding to the structure of the plunger 9, a first reduced diameter portion 16a, a second reduced diameter portion 16b, and a third reduced diameter portion 16c are formed on an inner surface of a liquid discharge hole 15 inside the tapered tube 3 of the barrel 1, and the structure of the first reduced diameter portion 16a, the second reduced diameter portion 16b, and the third reduced diameter portion 16c is formed such that a diameter thereof is gradually reduced and intervals 20a and 20b between reduced diameter portions are shortened as the tapered tube 3 goes frontward. Accordingly, the tapered tube 3 may correspond and be coupled to the plunger 9.

In the syringe having the above described structure, when the injection needle 12 is injected into a separate medicinal liquid container and the plunger rod 6 is pulled as usual use of a syringe, the plunger 9 fastened to the front end of the plunger rod 6 moves rearward along the inside of the barrel 1 and liquid medicine is filled into the barrel 1. When the barrel 1 is filled with the liquid medicine, the plunger rod 6 is pushed while the injection needle 12 is inserted in the skin of a patient, and the plunger 9 is moved forward along the inside of the barrel 1 to push the injection liquid filled in the barrel to be discharged through the injection needle 12, thereby completing the injection. When the plunger 9 reaches an end of the barrel 1, the plunger 9 is fully inserted into the discharge hole 15 inside the tapered tube 3 of the barrel 1.

As the first step 14a, the second step 14b, and the third step 14c of the plunger 9 are brought into contact with the first reduced diameter portion 16a, the second reduced diameter portion 16b, and the third reduced diameter portion 16c formed in the discharge hole 15 inside the tapered tube 3 of the barrel 1 in order, all the remaining injection is discharged through the injection needle 12. The plunger 9 is formed in the long conical shape and has the multiple-step structure consisting of a plurality of steps in which intervals 18a and 18b between the steps are shortened as the plunger goes frontward, so that the reaction pressure applied to the plunger 9 is reduced by distributing the pressure in order. Accordingly, the injection liquid may be easily injected with smooth and constant pressure until the end of the injection without giving pain to the patient, and the entire amount of injection liquid may be injected without injection liquid remaining.

In the present disclosure, the multi-layer reduced diameter portions formed on the inner surface of the discharge hole 15 inside the tapered tube 3 of the barrel 1 and the multi-layer steps formed on the plunger 9 are exemplified by three steps as an optimal preferred embodiment. However, the reduced diameter portions and the steps may be formed in two, four, or more steps in response to the size and capacity of the syringe. The present disclosure may be applied by variously designing and modifying intervals between steps, a bevel angle of a step, etc. to suit the situation.

Although the invention is described with reference to specific items such as specific structural elements, to merely some embodiments, and to drawings, such specific details disclosed herein are merely representative for purposes of helping more comprehensive understanding of the present disclosure. The present disclosure, however, is not limited to only the example embodiments set forth herein, and those skilled in the art will appreciate that the present disclosure can be embodied in many alternate forms.

Accordingly, the present disclosure is intended to cover not only the exemplary embodiments, but also various alternatives, modifications, equivalents and other embodiments that may be included within the spirit and scope of the present disclosure as defined by the appended claims.

What is claimed is:

1. A syringe with a plunger reaction pressure reduction structure, the syringe comprising:

a barrel (1) comprising a finger grip (2) at a rear end of the barrel (1) and a Luer-lock connector (4) at a front discharge end of the barrel (1), in which a thread portion (5) is formed on an inner surface of the Luer-lock connector outside a tapered tube (3);

a plunger rod (6) inserted into the barrel (1) and comprising a push end (7) at a rear end of the plunger rod (6);

a plunger (9) coupled to a front end of the plunger rod (6), the plunger (9) comprising a first step (14a), a second step (14b), a third step (14c), a rear interval (18a) between the first step (14a) and the second step (14b), and a front interval (18b) between the second step (14b) and the third step (14c); and a needle hub (11) screwed and fastened with the Luer-lock connector (4) and comprising an injection needle (12) mounted to a front end of the needle hub (11), wherein the plunger (9) is formed in a tapered conical shape; an outer diameter of the plunger (9) is gradually reduced along a longitudinal direction as the plunger (9) goes frontward; an inner surface of an inside liquid discharge hole (15) of the tapered tube (3) of the barrel (1) correspondingly coupled to the plunger (9) is configured such that an inner diameter of the inner surface of the inside liquid discharge hole (15) of the tapered tube (3) of the barrel (1) is gradually decreased as the tapered tube (3) goes frontward; and the inner surface of the inside liquid discharge hole (15) comprises a first reduced diameter portion (16a), a second reduced diameter portion (16b), a third reduced diameter portion (16c), a front interval (20b) between the second reduced diameter portion (16b) and the third reduced diameter portion (16c), and a rear interval (20a) between the first reduced diameter portion (16a) and the second reduced diameter portion (16b), thereby allowing the plunger (9) to correspondingly be coupled to the inner surface of the inside liquid discharge hole (15) of the tapered tube (3) of the barrel (1).

2. The syringe of claim 1, wherein the front interval (18b) between the second step (14b) and the third step (14c) is shorter than the rear interval (18a) between the first step (14a) and the second step (14b).

3. The syringe of claim 1, wherein the front interval (20b) between the second reduced diameter portion (16b) and the third reduced diameter portion (16c) is shorter than the rear interval (20a) between the first reduced diameter portion (16a) and the second reduced diameter portion (16b).

* * * * *